United States Patent [19]

Cheng

[11] 4,291,054
[45] Sep. 22, 1981

[54] INSECTICIDAL CARBAMOYL SULFIDES

[75] Inventor: Jiin-Duey Cheng, Wilmington, Del.

[73] Assignee: E. I. Du Pont de Nemours and Company, Wilmington, Del.

[21] Appl. No.: 101,799

[22] Filed: Dec. 10, 1979

[51] Int. Cl.³ ............... A01N 43/08; A01N 37/28; C07D 307/77; C07D 307/82

[52] U.S. Cl. ............... 424/298; 260/453 RW; 260/396 N; 260/346.22; 260/346.73; 424/285

[58] Field of Search ...... 260/453 RW, 396 N, 346.22, 260/346.73; 424/298, 285

[56] References Cited

U.S. PATENT DOCUMENTS 4,004,031  1/1977  Drabek ........................... 424/298

FOREIGN PATENT DOCUMENTS 848911  11/1976  Belgium ..................... 260/453 RW
848912  11/1976  Belgium ..................... 260/453 RW
848913  11/1976  Belgium ..................... 260/453 RW
2654282  11/1976  Fed. Rep. of Germany ...... 260/453 RW

OTHER PUBLICATIONS

Journal of Organic Chemistry, vol. 21, No. 11, 12-10-56, pp. 1201-1210.
Chem. Abs., vol. 76, 1972, 149972v, 24717j, 112752x; vol. 83, 1975, 116600p; vol. 84, 121,204n, vol.85, 20640s.
Chem. Abs., vol. 86, 1977, 139656n; vol. 87, 1977, 200835j, 201,132g; vol. 88, 1978, 6344d, 190124f, vol. 89, 1978, 215142w.
Chem. Abs., vol. 90, 1979, 86767y.

*Primary Examiner*—John M. Ford
*Assistant Examiner*—Robert C. Whittenbaugh

[57] ABSTRACT

4-Oxo-2,5-cyclohexadien-1-ylideneaminooxy derivatives, such as N-[[[N-[[N-[3,5-bis(1,1-dimethylethyl)-4-oxo-2,5-cyclohexadien-1-ylidenaminooxycarbonyl]-N-methylaminothio]]-N-methylaminocarbonyloxy]]]ethanimidothioic acid, methyl ester, useful for control of insects.

52 Claims, No Drawings

INSECTICIDAL CARBAMOYL SULFIDES

BACKGROUND OF THE INVENTION

This invention relates to carbamoyl sulfides useful as insecticides.

Belgian Pat. No. 848,911 discloses asymmetric insecticidal N-substituted bis-carbamoyl sulfides of the formula

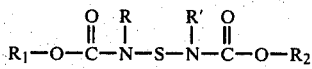

where R, R', $R_1$ and $R_2$ are as defined in the publication.

Belgian Pat. No. 848,912 discloses symmetrical insecticidal N-substituted bis-carbamoyl sulfides of the formula

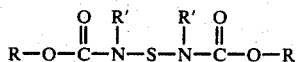

where R and R' are as defined in the publication.

Belgian Pat. No. 848,913 discloses insecticidal oxime thiobis-carbamates of the formula

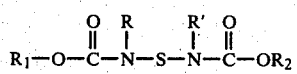

where R, R', $R_1$ and $R_2$ are as defined in the patent.

The compounds taught in these patents are active insecticides. Nevertheless, the need of new, highly active insecticides still exist. The use of active insecticides for the protection of beneficial crops is one way to resolve the world-wide food shortage.

The novel 4-oxo-2,5-cyclohexadien-1-ylideneaminooxy derivatives of this invention are highly active insecticides especially on Lepidoptera species such as tobacco budworm and southern armyworm. These compounds provide long residual activity with little or no redding of cotton.

SUMMARY OF THE INVENTION

This invention relates to novel 4-oxo-2,5-cyclohexadien-1-ylideneaminooxy derivatives of Formula I, to novel 2-oxo-3,5-cyclohexadien-1-yl-ideneaminooxy derivatives of Formula IX, to agricultural compositions containing them and to their method of use as insecticides.

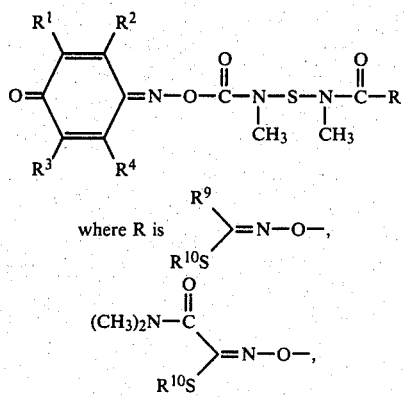

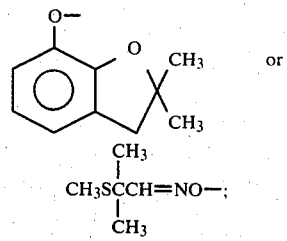

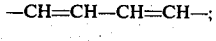

$R^1$, $R^2$, $R^3$, and $R^4$ are independently H, F, Cl, Br, $NO_2$, CN, $CF_3$, $C_1$-$C_{12}$ alkyl, $C_1$-$C_4$ alkoxy, or $COR^5$;
$R^5$ is $OR^6$ or $NR^7R^8$;
$R^6$ is $C_1$-$C_4$ alkyl;
$R^7$ is $C_1$-$C_4$ alkyl or methoxy;
$R^8$ is $C_1$-$C_4$ alkyl;
$R^9$ and $R^{10}$ are independently methyl or ethyl; or
$R^1$ and $R^2$ are taken together to form

—CH=CH—CH=CH—;

provided that:

(1) The total of $R^9$ and $R^{10}$ is not greater than three carbon atoms;

(2) Only one of $R^1$, $R^2$, $R^3$ and $R^4$ can be CN, $NO_2$, $COR^5$, or $CF_3$;

(3) If $R^2$ and $R^4$ are both alkyl, then $R^2$ and $R^4$ are independently $CH_3$ or $CH_2CH_3$;

(4) If any two of $R^1$, $R^2$, $R^3$, and $R^4$ are independently halogen or alkoxy, then the other two are independently hydrogen or $CH_3$;

(5) The total number of carbons $R^1$ to $R^4$ is not greater than 26;

(6) If $R^1$ and $R^2$ are both alkyl, then $R^2$ must be $CH_3$ or $CH_2CH_3$;

(7) If $R^3$ and $R^4$ are both alkyl, then $R^4$ must be $CH_3$ or $CH_2CH_3$.

The compounds of formula IX are of the formula

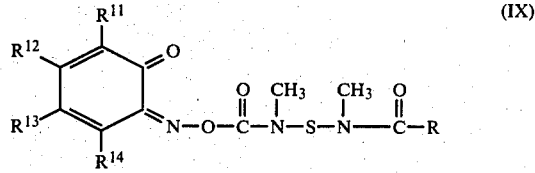

wherein
R is as previously defined including definitions of $R^9$ and $R^{10}$;
$R^{11}$, $R^{12}$, $R^{13}$ and $R^{14}$ are independently, H, $C_1$-$C_{12}$ alkyl, $C_1$-$C_4$ alkoxy, Cl or Br; or
either $R^{11}$ and $R^{12}$ or $R^{13}$ and $R^{14}$ are taken together to form —CH=CH—CH=CH—;
provided that
(1) the total of $R^9$ and $R^{10}$ is not greater than three carbon atoms;
(2) if three or more of $R^{11}$, $R^{12}$, $R^{13}$ and $R^{14}$ are other than H, then any of $R^{11}$, $R^{12}$, $R^{13}$ and $R^{14}$ which is not H, is selected from $CH_3$ or Cl, except that if $R^{11}$ and $R^{12}$ or $R^{13}$ and $R^{14}$ form the bridge —CH=CH—CH=CH—, then the remaining $R^{11}$ to $R^{14}$ groups are chosen from all definitions of $R^{11}$ to $R^{14}$;
(3) if any of $R^{11}$, $R^{12}$, $R^{13}$ and $R^{14}$ is secondary alkyl, tertiary alkyl or tertiary alkoxy, the adjacent group which is at least one of $R^{11}$, $R^{12}$, $R^{13}$ or $R^{14}$ must be selected from H, $CH_3$ or $CH_2CH_3$;

(4) the total number of carbons of $R^{11}$ to $R^{14}$ is not greater than 16.

Also, this invention relates to novel intermediates of the formulae

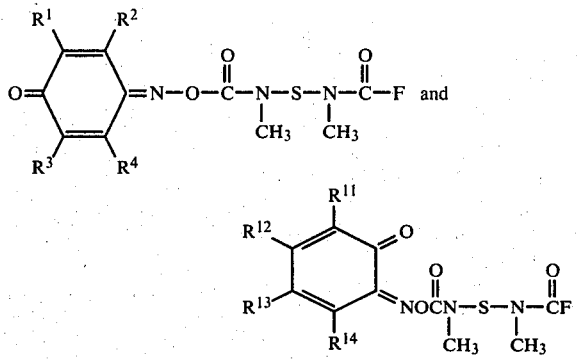

where $R^1$, $R^2$, $R^3$, $R^4$, $R^{11}$, $R^{12}$, $R^{13}$ and $R^{14}$ are as previously defined.

PREFERRED COMPOUNDS

Preferred for their ease of synthesis are those compounds of Formulae I and IX where $R^1$ and $R^4$ are independently H, Cl, F, $C_1$-$C_5$ alkyl, $C_1$-$C_3$ alkoxy, or $CO_2R^6$ where $R^6$ is $C_1$-$C_4$ alkyl; $R^{11}$ to $R^{14}$ are independently H, Cl, $C_1$-$C_5$ alkyl and $C_1$-$C_3$ alkoxy.

More preferred for higher insecticidal activity are those compounds of the preferred scope wherein $R^9$ and $R^{10}$ are $CH_3$.

Most preferred for even higher insecticidal activity are those compounds of the more preferred scope wherein $R^2$ and $R^4$ are H and $R^1$ and $R^3$ are independently $C_1$-$C_5$ alkyl; $R^{12}$ and $R^{14}$ are H and $R^{11}$ and $R^{13}$ are independently $C_1$-$C_5$ alkyl.

Specifically preferred for high insecticidal activity are the compounds:

N-[[[N-[N-[3,5-bis(1,1-dimethylethyl)-4-oxo-2,5-cyclohexadien-1-ylideneaminooxycarbonyl]-N-methylaminothio]]-N-methylaminocarbonyloxy]]-ethanimidothioic acid, methyl ester N-[N-[N-(3,5-dimethyl-4-oxo-2,5-cyclohexadien-1-ylideneaminooxycarbonyl)-N-methylaminothio]-N-methylaminocarbonyloxy]ethanimidothioic acid, methyl ester N-[N-methyl-N-[N-methyl-N-[2-methyl-5-(1-methylethyl)-4-oxo-2,5-cyclohexadien-1-ylideneaminooxycarbonyl]-aminothio]aminocarbonyloxy]-ethanimidothioic acid, methyl ester N-[N-[N-[3,5-bis(1-methylpropyl)-4-oxo-2,5-cyclohexadien-1-ylideneaminooxycarbonyl]-N-methylaminothio]-N-methylaminocarbonyloxy]-ethanimidothioic acid, methyl ester N-[N-[N-[3,5-bis(1-methylethyl)-4-oxo-2,5-cyclohexadien-1-ylideneaminooxycarbonyl]-N-methylaminothio]-N-methylcarbonyloxy]-ethanimidothioic acid, methyl ester methyl N-[N-[N-[[3,5-bis(1,1-dimethylethyl)-6-oxo-2,4-cyclohexadien-1-ylidene]aminoxycarbonyl]-N-methylaminothio]-N-methylaminocarbonyloxy]e-thanimidothioate methyl N-[N-[N-[(3-dodecyl-1,4-dihydro-4-oxo-1-naphthaleneidene)aminooxycarbonyl]-N-methylaminothio]-N-methylaminocarbonyloxy]e-thanimidothioate methyl N-[N-[N-[(1,2-dihydro-1-oxo-2-naphthalenylidene)aminooxycarbonyl]-N-methylaminothio]-N-methylaminocarbonyloxy]e-thanimidothioate methyl N-[N-[N-[(1,4-dihydro-3-methyl-4-oxo-1-naphthalenylidene)aminooxycarbonyl]-N-methylaminothio]-N-methylaminocarbonyloxy]-ethanimidothioate

SYNTHESIS

Novel compounds of this invention can be prepared by the reaction of the carbamoyl fluoride of Formula IV and a nitrosophenol of Formula V as shown in Scheme I:

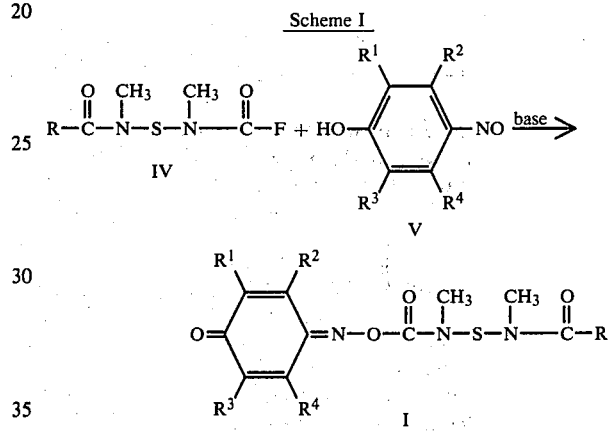

where R, $R^1$, $R^2$, $R^3$ and $R^4$ are as defined in the previous section. An acid scavenger is normally employed, and either an organic base such as triethylamine, pyridine, dialkylaniline or an inorganic base such as potassium hydroxide or potassium carbonate can be used. The reaction temperature can be varied from −20° to 80° C. in a period of 10 minutes to 24 hours. An aprotic solvent such as ether, toluene, methylene chloride, etc. can be chosen as the reaction medium. It is preferred that the reaction be conducted in diethyl ether or toluene at ambient temperature for 30 minutes to 4 hours in the presence of triethylamine.

Compounds of Formula I can also be prepared by the reaction of Compound IV and an anion of the nitrosophenol (V), generated by a base such as sodium hydride, in an aprotic solvent, preferably in dry tetrahydrofuran at −20° to 30° C.

An alternative way for preparing compounds of Formula I can be illustrated as shown in Scheme II.

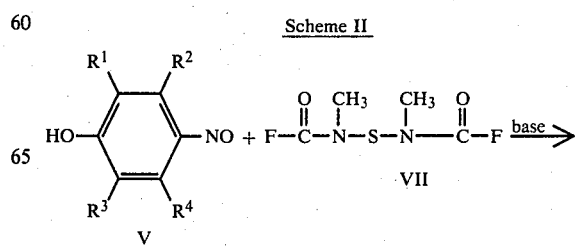

-continued
Scheme II

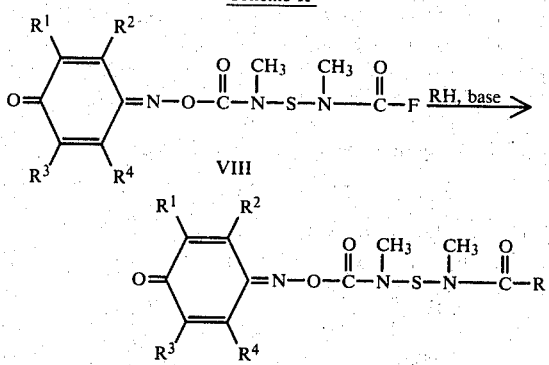

wherein R, R¹, R², R³ and R⁴ were defined in the previous section.

The reaction of the nitrosophenol (V) and VII can be carried out in an aprotic solvent such as diethyl ether, tetrahydrofuran, methylene chloride, toluene or a mixed solvent at −20° to 30° C. for 30 minutes to 5 hours. An organic tertiary amine such as triethylamine is preferred to be the acid acceptor. Under the similar reaction conditions, compounds of Formula I can be prepared by the reaction of VIII and RH. However, either an organic tertiary amine or an inorganic hydroxide or carbonate can be chosen as acid acceptor.

Novel compounds of Formula IX can be obtained either from the reaction of an o-nitrosophenol and the carbamoyl fluoride of Formula IV

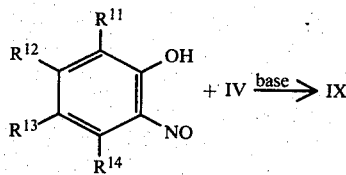

or from the reaction of compounds of Formula X and RH under similar conditions under which compounds of Formula I were prepared. Compounds of Formula X can be synthesized by the reaction of an o-nitrosophenol and compound VII as described for the preparation of compound VIII.

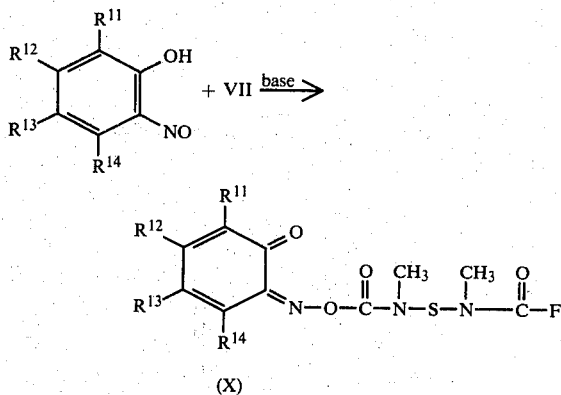

The preparation of o-nitrosophenols has been described in the literature [cf., *Acta Chim. Acad. Sci. Hung.*, 98, 327 (1978)] and references cited therein.

The nitrosophenol (V) exhibits the character of a quinone monoxime. The tautomerization has been well documented [J. Org. Chem., 21, 1201 (1956)].

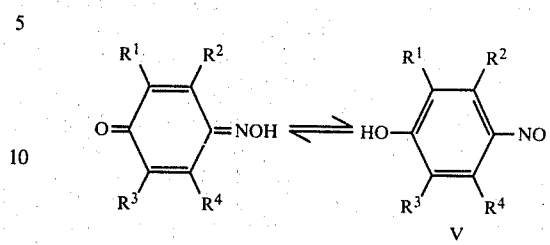

The carbamoyl fluorides of Formula IV and VII can be prepared by the methods taught in DT No. 2654282.

In the above reaction procedures, pressure is not critical, but for convenience, atmospheric pressure is preferred.

The preparation of compounds in this invention can be more clearly demonstrated by the following examples. Unless otherwise stated, all temperatures are in degrees Centigrade and parts are by weight.

EXAMPLE 1

N-[[[N-[[3,5-bis(1,1-dimethylethyl)-4-oxo-2,5-cyclohexadien-1-ylideneaminooxycarbonyl]-N-methylaminothio]]-N-methylaminocarbonyloxy]]-ethanimidothioic acid, methyl ester A solution of 1.2 g of triethylamine in 10 ml of dry ether was added dropwise to a mixture of 2.4 g of 2,6-di-t-butyl-4-nitrosophenol and 2.7 g of N-[[[N-[[N-fluorocarbonyl-N-methylaminothio]]-N-methylaminocarbonyloxy]]]ethanimidothioic acid methyl ester suspended in 40 ml of dry ether at a temperature below 25°. The mixture was stirred at room temperature for 50 minutes. Then, water and hexane were added to the mixture. The product was collected by filtration, washed with water, hexane, and air-dried to give 4.1 g of N-[[[N-[[3,5-bis-(1,1-dimethylethyl)-4-oxo-2,5-cyclohexadien-1-yli-deneaminooxycarbonyl]-N-methylaminothio]]-N-methylaminocarbonyloxy]]ethanimidothioic acid methyl ester, m.p. 160°–161.6°.

EXAMPLE 2

[[[N-[[3,5-bis[1,1-dimethylethyl]-4-oxo-2,5-cyclohexadien-1-ylideneaminooxycarbonyl]]-N-methylaminothio]]-]methylcarbamic fluoride A solution of 2.1 g of triethylamine in 10 ml of dry ether was added dropwise to a suspension of 4.7 g of 2,6-di-tert-butyl-4-nitrosophenol and 3.8 g of N,N'-thiobis[N-methylcarbamic fluoride] in a mixture of 60 ml of dry methylene chloride and 20 ml of ether at 0° to 5°. A clear solution was obtained after the addition. The mixture was stirred on an ice bath for 3 hours and hexane was added. The mixture was washed with water twice, dried over anhydrous magnesium sulfate and filtered. The filtrate was evaporated to give an oil which was crystallized from cold hexane to yield 4.1 g of [[[N-[[3,5-bis[1,1-dimethylethyl]-4-oxo-2,5-cyclohexadien-1-ylideneaminooxycarbonyl]]-N-methylaminothio]]]methylcarbamic fluoride, m.p. 109.5°–113°.

EXAMPLE 3

N-[[[[N-[[[N-[[3,5-bis[1,1-dimethylethyl]-4-oxo-2,5-cyclohexadien-1-ylideneaminooxycarbonyl]]N-methylaminothio]]]-N-methylaminocarbonyloxy]]]]-2-dimethylamino]-2-oxo-ethanimidothioic acid, methyl ester A mixture of 3.2 g of [[[N-[[3,5-bis[1,1-dimethylethyl]-4-oxo-2,5-cyclohexadien-1-ylideneaminooxycarbonyl]]-N-methylaminothio]]]methylcarbamic fluoride, 1.4 g of N,N-dimethyl-2-hydroximino-2-methylthioacetamide and 1 g of triethylamine in 30 ml of dry ether was stirred at room temperature for 2 hours. Hexane and water were added. The organic phase was removed under vacuum. The crude product was obtained by filtration and recrystallized from hexane-ether mixture to give 3.4 g of N-[[[[N-[[[N-[[3,5-bis[1,1-dimethylethyl]-4-oxo-2,5-cyclohexadien-1-ylideneaminooxycarbonyl]]-N-methylaminothio]]]-N-methylaminocarbonyloxy]]]]-2-dimethylamino]-2-oxo-ethanimidothioic acid methyl ester, m.p. 155°–159°.

The novel compounds of this invention can be prepared by the methods set forth including but not restricted by the following examples.

TABLE 1

Structure: $R^1, R^2, R^3, R^4$ substituted cyclohexadienone $=N-O-C(=O)-N(CH_3)-S-N(CH_3)-C(=O)-O-N=C(R^9)(SR^{10})$

| $R^1$ | $R^2$ | $R^3$ | $R^4$ | $R^9$ | $R^{10}$ | melting point °C. |
|---|---|---|---|---|---|---|
| CH₃ | H | CH₃ | H | CH₃ | CH₃ | 175.5–178 |
| i-Pr | H | H | CH₃ | CH₃ | CH₃ | 90–99 |
| sec-Bu | H | sec-Bu | H | CH₃ | CH₃ | 103–106 |
| i-Pr | H | i-Pr | H | CH₃ | CH₃ | 120.5–121.5 |
| H | t-Bu | t-Bu | H | CH₃ | CH₃ | 178–179.5 |
| Cl | H | Cl | H | CH₃ | CH₃ | 140–142(dec.) |
| H | H | H | H | CH₃ | CH₃ | 174–177(dec.) |
| H | Cl | H | Cl | CH₃ | CH₃ | |
| H | Cl | Cl | H | CH₃ | CH₃ | |
| F | H | F | H | CH₃ | CH₃ | |
| H | F | H | H | CH₃ | CH₃ | |
| CH₃ | H | H | F | CH₃ | CH₃ | |
| Br | H | H | Br | CH₃ | CH₃ | |
| H | Br | H | H | CH₃ | CH₃ | |
| H | H | Br | H | CH₃ | CH₃ | |
| CH₃ | CH₃ | CH₃ | CH₃ | CH₃ | CH₃ | 162.5–166.5 |
| H | Et | H | Et | CH₃ | CH₃ | |
| H | CH₃ | CH₃ | H | CH₃ | CH₃ | 131.5–133.5 |
| CH₃ | NO₂ | H | H | CH₃ | CH₃ | |
| H | H | NO₂ | CH₃ | CH₃ | CH₃ | |
| NO₂ | H | H | CH₃ | CH₃ | CH₃ | |
| H | H | H | NO₂ | CH₃ | CH₃ | |
| CN | H | H | H | CH₃ | CH₃ | |
| H | CN | H | H | CH₃ | CH₃ | |
| t-Bu | H | t-Bu | CN | CH₃ | CH₃ | |
| CH₃ | H | CN | CH₃ | CH₃ | CH₃ | |
| CF₃ | H | H | H | CH₃ | CH₃ | |
| H | CF₃ | H | H | CH₃ | CH₃ | |
| —CH=CH—CH=CH— | | n-C₁₂H₂₅— | H | CH₃ | CH₃ | 87–88.5 |
| —CH=CH—CH=CH— | | CH₃ | H | CH₃ | CH₃ | 156–159(dec.) |
| Cl | H | H | CF₃ | CH₃ | CH₃ | |
| H | Cl | CF₃ | H | CH₃ | CH₃ | |
| CH₃O | H | CH₃O | H | CH₃ | CH₃ | |
| n-BuO | H | n-BuO | H | CH₃ | CH₃ | |
| H | CH₃O | CH₃O | H | CH₃ | CH₃ | |
| H | n-BuO | n-BuO | H | CH₃ | CH₃ | |
| H | H | H | CH₃O | CH₃ | CH₃ | |
| H | H | H | n-BuO | CH₃ | CH₃ | |
| n-C₁₂H₂₅ | H | H | H | CH₃ | CH₃ | |
| H | n-C₁₂H₂₅ | H | H | CH₃ | CH₃ | |
| H | CH₃ | n-C₁₂H₂₅ | H | CH₃ | CH₃ | |
| CH₃ | H | H | n-C₁₂H₂₅ | CH₃ | CH₃ | |
| CH₃ | H | CO₂CH₃ | H | CH₃ | CH₃ | |
| CH₃ | H | CO₂t-Bu | H | CH₃ | CH₃ | |
| CH₃ | H | CONMe₂ | H | CH₃ | CH₃ | |
| CH₃ | H | CON(n-Bu)₂ | H | CH₃ | CH₃ | |
| CH₃ | H | CON(OCH₃)CH₃ | H | CH₃ | CH₃ | |
| CO₂CH₃ | H | Et | H | CH₃ | CH₃ | |
| CO₂n-Bu | H | Et | H | CH₃ | CH₃ | |
| CONMe₂ | H | Et | H | CH₃ | CH₃ | |
| CON(n-Bu)₂ | H | Et | H | CH₃ | CH₃ | |
| CON(OMe)Me | H | Et | H | CH₃ | CH₃ | |
| H | CO₂CH₃ | H | H | CH₃ | CH₃ | |
| H | CO₂n-Bu | H | H | CH₃ | CH₃ | |
| H | CONMe₂ | H | H | CH₃ | CH₃ | |
| H | CON(n-Bu)₂ | H | H | CH₃ | CH₃ | |
| H | CON(OMe)Me | H | H | CH₃ | CH₃ | |

TABLE 1-continued

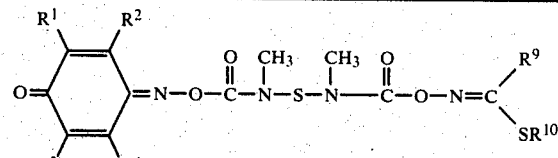

| R¹ | R² | R³ | R⁴ | R⁹ | R¹⁰ | melting point °C. |
|---|---|---|---|---|---|---|
| Cl | H | H | CO$_2$CH$_3$ | CH$_3$ | CH$_3$ | |
| Cl | H | H | CO$_2$n-Bu | CH$_3$ | CH$_3$ | |
| Cl | H | H | CONMe$_2$ | CH$_3$ | CH$_3$ | |
| Cl | H | H | CON(n-Bu)$_2$ | CH$_3$ | CH$_3$ | |
| H | H | H | CO(OMe)Me | CH$_3$ | CH$_3$ | |
| t-Bu | H | t-Bu | H | Et | CH$_3$ | |
| t-Bu | H | CH$_3$ | H | CH$_3$ | CH$_3$ | 136–139 |
| t-Bu | H | t-Bu | H | CH$_3$ | Et | |
| sec-Bu | H | sec-Bu | H | CH$_3$ | Et | |
| H | t-Bu | t-Bu | H | CH$_3$ | Et | |
| CH$_3$ | H | CH$_3$ | H | CH$_3$ | Et | |
| EtC(CH$_3$)$_2$ | H | EtC(CH$_3$)$_2$ | H | CH$_3$ | CH$_3$ | |
| t-Bu | H | H | CH$_3$ | CH$_3$ | CH$_3$ | 106–110(dec.) |

TABLE 2

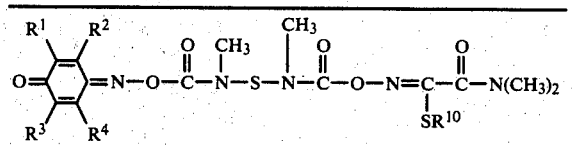

| R¹ | R² | R³ | R⁴ | R¹⁰ | melting point °C. |
|---|---|---|---|---|---|
| t-Bu | H | H | H | CH$_3$ | |
| sec-Bu | H | sec-Bu | H | CH$_3$ | |
| t-Bu | H | t-Bu | H | Et | |
| H | CH$_3$ | i-Pr | H | CH$_3$ | |
| CH$_3$ | H | CH$_3$ | H | CH$_3$ | |
| EtC(CH$_3$)$_2$— | H | EtC(CH$_3$)$_2$— | H | CH$_3$ | |
| CH$_3$ | CH$_3$ | CH$_3$ | CH$_3$ | CH$_3$ | |
| H | t-Bu | t-Bu | H | CH$_3$ | |
| Cl | H | Cl | H | CH$_3$ | |
| i-Pr | H | i-Pr | H | CH$_3$ | |

TABLE 3

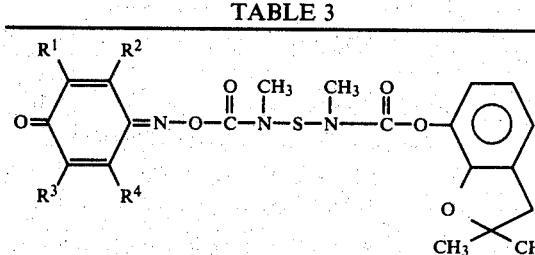

| R¹ | R² | R³ | R⁴ | melting point °C. |
|---|---|---|---|---|
| t-Bu | H | t-Bu | H | |
| H | t-Bu | t-Bu | H | |
| EtC(CH$_3$)$_2$ | H | EtC(CH$_3$)$_2$ | H | |

TABLE 3-continued

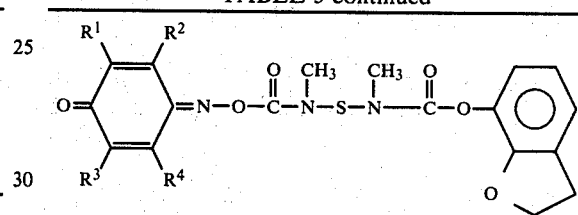

| R¹ | R² | R³ | R⁴ | melting point °C. |
|---|---|---|---|---|
| CH$_3$ | H | CH$_3$ | H | |
| CH$_3$ | CH$_3$ | CH$_3$ | CH$_3$ | |
| sec-Bu | H | sec-Bu | H | |
| H | H | t-Bu | H | |
| i-Pr | H | i-Pr | H | |
| H | CH$_3$ | i-Pr | H | |

TABLE 4

| R¹ | R² | R³ | R⁴ | melting point °C. |
|---|---|---|---|---|
| t-Bu | H | t-Bu | H | oil |
| EtC(CH$_3$)$_2$ | H | EtC(CH$_3$)$_2$ | H | |
| sec-Bu | H | sec-Bu | H | |
| CH$_3$ | H | CH$_3$ | H | |
| i-Pr | H | i-Pr | H | |
| CH$_3$ | CH$_3$ | CH$_3$ | CH$_3$ | |
| t-Bu | H | H | t-Bu | |
| i-Pr | H | H | CH$_3$ | |

TABLE 5

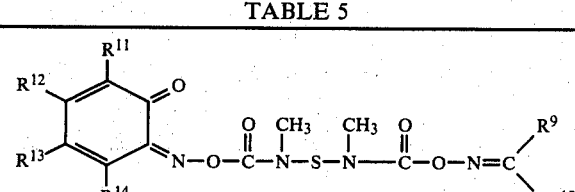

| R¹¹ | R¹² | R¹³ | R¹⁴ | R⁹ | R¹⁰ | melting point °C. |
|---|---|---|---|---|---|---|
| t-Bu | H | t-Bu | H | CH$_3$ | CH$_3$ | 142–145 |
| t-Bu | H | H | t-Bu | CH$_3$ | CH$_3$ | |
| H | H | Cl | H | CH$_3$ | CH$_3$ | |
| H | Br | Br | H | CH$_3$ | CH$_3$ | |

TABLE 5-continued

Structure:

$$R^{11}, R^{12}, R^{13}, R^{14}\text{-substituted quinone}=N-O-\overset{O}{\underset{\|}{C}}-\underset{|}{\overset{CH_3}{N}}-S-\underset{|}{\overset{CH_3}{N}}-\overset{O}{\underset{\|}{C}}-O-N=\overset{R^9}{\underset{SR^{10}}{C}}$$

| $R^{11}$ | $R^{12}$ | $R^{13}$ | $R^{14}$ | $R^9$ | $R^{10}$ | melting point °C. |
|---|---|---|---|---|---|---|
| Cl | H | Cl | H | $CH_3$ | $CH_3$ | |
| Br | H | Br | H | $CH_3$ | $CH_3$ | |
| H | Cl | Cl | H | $CH_3$ | $CH_3$ | |
| $CH_3$ | Cl | $CH_3$ | Cl | $CH_3$ | $CH_3$ | |
| $CH_3$ | $CH_3$ | $CH_3$ | $CH_3$ | $CH_3$ | $CH_3$ | |
| $CH_3$ | H | $CH_3$ | Br | $CH_3$ | $CH_3$ | |
| $n$-$C_{12}H_{25}$ | H | H | H | $CH_3$ | $CH_3$ | |
| H | H | $n$-$C_{12}H_{25}$ | H | $CH_3$ | $CH_3$ | |
| $CH_3$ | H | H | $n$-$C_{12}H_{25}$ | $CH_3$ | $CH_3$ | |
| $CH_3O$ | H | $CH_3$ | H | $CH_3$ | $CH_3$ | |
| $n$-BuO | H | $CH_3$ | H | $CH_3$ | $CH_3$ | |
| $CH_3$ | H | $CH_3O$ | H | $CH_3$ | $CH_3$ | |
| $CH_3$ | H | $n$-BuO | H | $CH_3$ | $CH_3$ | |
| Cl | H | Cl | $CH_3O$ | $CH_3$ | $CH_3$ | |
| Cl | H | Cl | $n$-BuO | $CH_3$ | $CH_3$ | |
| $CH_3$ | $CH_3O$ | H | H | $CH_3$ | $CH_3$ | |
| $CH_3$ | $n$-BuO | H | H | $CH_3$ | $CH_3$ | |
| $t$-Bu | H | $t$-Bu | H | $CH_3$ | Et | |
| $t$-Bu | H | $t$-Bu | H | Et | $CH_3$ | |
| —CH=CH—CH=CH— | | H | H | $CH_3$ | $CH_3$ | 140–144(dec.) |
| H | H | —CH=CH—CH=CH— | | $CH_3$ | $CH_3$ | 148–152(dec.) |

TABLE 6

Structure:

$$R^{11}, R^{12}, R^{13}, R^{14}\text{-substituted quinone}=N-O-\overset{O}{\underset{\|}{C}}-\underset{|}{\overset{CH_3}{N}}-S-\underset{|}{\overset{CH_3}{N}}-\overset{O}{\underset{\|}{C}}-O-N=\overset{\overset{O}{\underset{\|}{CN(CH_3)_2}}}{\underset{S-R^{10}}{C}}$$

| $R^{11}$ | $R^{12}$ | $R^{13}$ | $R^{14}$ | $R^{10}$ | melting point °C. |
|---|---|---|---|---|---|
| $t$-Bu | H | $t$-Bu | H | $CH_3$ | |
| $t$-Bu | H | H | $t$-Bu | $CH_3$ | |
| $CH_3$ | $CH_3$ | $CH_3$ | $CH_3$ | $CH_3$ | |
| $t$-Bu | H | $t$-Bu | H | Et | |
| Cl | H | Cl | H | $CH_3$ | |

TABLE 7

Structure:

$$R^{11}, R^{12}, R^{13}, R^{14}\text{-substituted quinone}=N-O-\overset{O}{\underset{\|}{C}}-\underset{|}{\overset{CH_3}{N}}-S-\underset{|}{\overset{CH_3}{N}}-\overset{O}{\underset{\|}{C}}-O-N=CH-\overset{CH_3}{\underset{CH_3}{\overset{|}{C}}}-S-CH_3$$

| $R^{11}$ | $R^{12}$ | $R^{13}$ | $R^{14}$ | melting point °C. |
|---|---|---|---|---|
| $t$-Bu | H | $t$-Bu | H | |
| $t$-Bu | H | H | $t$-Bu | |
| $CH_3$ | $CH_3$ | $CH_3$ | $CH_3$ | |
| Cl | H | Cl | H | |
| Cl | $CH_3$ | $CH_3$ | H | |
| H | $CH_3$ | Cl | $CH_3$ | |

TABLE 8

Structure:

$$R^{11}, R^{12}, R^{13}, R^{14}\text{-substituted quinone}=N-O-\overset{O}{\underset{\|}{C}}-\underset{|}{\overset{CH_3}{N}}-S-\underset{|}{\overset{CH_3}{N}}-\overset{O}{\underset{\|}{C}}-O-\text{(benzofuranyl group)}$$

| $R^{11}$ | $R^{12}$ | $R^{13}$ | $R^{14}$ | melting point °C. |
|---|---|---|---|---|
| $t$-Bu | H | $t$-Bu | H | |
| $t$-Bu | H | H | $t$-Bu | |
| Cl | H | Cl | H | |
| Cl | $CH_3$ | $CH_3$ | H | |
| H | $CH_3$ | Cl | $CH_3$ | |
| $CH_3$ | H | $CH_3$ | H | |

FORMULATIONS

Useful formulations of the compounds of Formulae I and IX can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredeints in the approximate proportions set forth in Table 5.

TABLE 9

|  | Weight Percent* | | |
| --- | --- | --- | --- |
|  | Active Ingredient | Diluent(s) | Surfactant(s) |
| Wettable Powders | 20-90 | 0-74 | 1-10 |
| Oil Suspensions, Solutions, Emulsions (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active Ingredient plus at least one of Surfactant or a Diluent equals 100 weight percent.

Lower or higher levels of active ingredient can be present, depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer or fluid energy mill. Suspensions are prepared by wet milling (see, for example, Littler, U.S. Pat. No. 3,060,084). Granules and pellets can be made by spraying the active material on preformed granular carriers or by agglomeration techniques. See J. E. Browning, "Agglomeration", Chemical Engineering, Dec. 4, 1967, pp. 147ff and "Perry's Chemical Engineer's Handbook", 4th Ed., McGraw-Hill, New York, 1963, pp. 8-59ff.

For further information regarding the art of formulation, see for example: J. E. Browning, "Agglomeration", Chemical Engineering, Dec. 4, 1967 pp. 147ff and "Perry's Chemical Engineer's Handbook", 4th. Edn., McGraw-Hill, New York, 1963, pp. 8-59ff.

For further information regarding the art of formulation, see for example:

J. B. Buchanan, U.S. Pat. No. 3,576,834, Apr. 27, 1971, Col. 5 Line 36 through Col. 7, Line 70 and Ex. 1-4, 17, 106, 123-140.

R. R. Shaffer, U.S. Pat. No. 3,560,616, Feb. 2, 1971, Col. 3, Line 48 through Col. 7, Line 26 and Examples 3-9, 11-18. E. Somers, "Formulation", Chapter 6 in Torgeson, "Fungicides", Vol. I, Academic Press, New York, 1967.

EXAMPLE 4

| Wettable Powder | |
| --- | --- |
| N-[[[N-[[N-[3,5-bis(1,1-dimethylethyl)-4-oxo-2,5-cyclohexadien-1-ylidene-aminooxycarbonyl]-N-methyl-aminothio]]-N-methylamino-carbonyloxy]]]ethanimido-thioic acid, methyl ester | 40% |
| Dioctyl sodium sulfosuccinate | 1.5% |
| Sodium ligninsulfonate | 3% |
| Low viscosity methyl cellulose | 1.5% |
| Attapulgite | 54% |

The ingredients are thoroughly blended, passed through an air mill, to produce an average particle size under 15 microns, reblended, and sifted through a U.S.S.No. 50 sieve (0.3 mm opening) before packaging.

All compounds of the invention may be formulated in the same manner.

EXAMPLE 5

| Solution | |
| --- | --- |
| N-[[[N-[[N-[3,5-bis(1,1-dimethylethyl)-4-oxo-2,5-cyclohexadien-1-ylidene-aminooxycarbonyl]-N-methyl-amino]]-N-methylamino-carbonyloxy]]]ethanimido-thioic acid, methyl ester | 30% |
| Dimethylformamide | 70% |

The ingredients are combined and stirred to produce a solution, which can be used for low volume applications.

EXAMPLE 6

| Dust | |
| --- | --- |
| N-[[[N-[[N-[3,5-bis(1,1-dimethylethyl)-4-oxo-2,5-cyclohexadien-1-ylidene-aminooxycarbonyl]-N-methyl-amino]]-N-methylamino-carbonyloxy]]]ethanimido-thioic acid, methyl ester | 10% |
| Attapulgite | 10% |
| Pyrophyllite | 80% |

The active ingredient is blended with attapulgite and then passed through a hammer mill to produce particles substantially all below 200 microns. The ground concentrate is then blended with powdered pyrophyllite until homogeneous.

EXAMPLE 7

| Aqueous Suspension | |
| --- | --- |
| N-[[[N-[[N-[3,5-bis(1,1-dimethylethyl)-4-oxo-2,5-cyclohexadien-1-ylidene-aminooxycarbonyl]-N-methyl-amino]]-N-methylamino-carbonyloxy]]]ethanimido-thioic acid, methyl ester | 25% |
| Hydrated attapulgite | 3% |
| Crude calcium ligninsulfonate | 10% |
| Sodium dihydrogen phosphate | 0.5% |
| Water | 61.5% |

The ingredients are ground together in a ball or roller mill until the solid particles have been reduced to diameters under 10 microns.

EXAMPLE 8

| Wettable Powder | |
| --- | --- |
| N-[[[N-[[N-[3,5-bis(1,1-dimethylethyl)-4-oxo-2,5-cyclohexadien-1-ylidene-aminooxycarbonyl]-N-methyl-amino]]-N-methylamino-carbonyloxy]]]ethanimido-thioic acid, methyl ester | 50% |
| Sodium alkylnaphthalenesulfonate | 2% |
| Low viscosity methyl cellulose | 2% |
| Diatomaceous earth | 46% |

The ingredients are blended, coarsely hammermilled and then air milled to produce particles of active essentially all below 10 microns in diameter. The product is reblended before packaging.

EXAMPLE 9

| Granule | |
| --- | --- |
| Wettable powder of Example 8 | 10% |
| Attapulgite granules (U.S.S. # 20–40; 0.84–0.42 mm) | 90% |

A slurry of wettable powder containing 50% solids is sprayed on the surface of attapulgite granuels in a double-cone blender. The granules are dried and packaged.

USE

The compounds of this invention of Formulae I and IX have insecticidal activity on major agricultural, public health, and household pests.

The examples below demonstrate the control efficacy of these compounds.

These compounds have a wide spectrum of insecticidal activity, controlling economically significant pest species in the orders Lepidoptera, Homoptera, Diptera, and Coleoptera. More specifically, insects controlled by these compounds include, but are not limited to, the southern armyworm (*Spodoptera eridania*), bean aphid (*Aphis fabae*), housefly (*Musca domestica*), boll weevil (*Anthonomus grandis grandis*), and tobacco budworm (*Heliothis virescens*).

Control is achieved through application of one or more of the insecticidal compounds of this invention to the area to be protected, to the pests themselves, and/or the locus of infestation. The usual methods of application to agricultural crops, using compounds of this invention, are by foliar applications or applications to those plant parts which are to be protected. Applications, however, are not limited to these methods. The rate of application required for effective control is dependent upon both biological factors, e.g. the pest species, its life stage, size, and locations and upon non-biological factors, e.g. weather conditions (temperature, rainfall, humidity, etc.), time of year, application method, crop (plant growth habit and characteristics), and agronomic factors (crop spacing, soil type, etc.). In general, application rates of 0.07 to 8 kg/ha may be required for pest control in agriculture, the rates being dependent upon the above-listed biological and non-biological factors. However, rates of 0.14 to 2 kg/ha will, under normal circumstances, result in effective control. Rates of 0.28 to 1.5 kg/ha will normally be used in large scale field operations.

Compounds of this invention of Formulae I and IX can be mixed with insecticides, fungicides, nematicides, bactericides, acaricides, and/or other biologically active compounds, in order to achieve effective control with a minimum of input of material, time, and effort. The mixture ratio for each part by weight of compounds of this invention with the above-listed biologically active chemicals may vary from 0.20 to 5.00 parts by weight. The following list consists of a few select examples of chemicals presently employed in the above-listed control classes. The mixture composition, however, is not be be construed as being limited solely to the various possible combinations of those compounds.

Insecticides:

3-hydroxy-N-methylcrotonamide(dimethylphosphate)ester (Azodrin®) methylcarbamic acid, ester with 2,3-dihydro-2,2-dimethyl-7-benzofuranol (Furadan®)

O-[2,4,5-trichlore-a-(chloromethyl) benzyl] phosphoric acid, O',O'-dimethyl ester (Gardona ®)

2-mercaptosuccinic acid, diethyl ester, S-ester with thionophosphoric acid, dimethyl ester (Malathion ®)

phosphorothioic acid, O,O-dimethyl, O-p-nitrophenyl ester (methyl parathion)

methylcarbamic acid, ester with α-naphthol (Sevin ®)

methyl O-(methylcarbamoyl) thiolacetohydroxamate (methomyl)

N'-(4-chloro-o-tolyl)-N,N-dimethylformamidine (Galecron ®)

O,O - diethyl - O - (2-isopropyl - 4 - methyl - 6 - pyrimidyl-phosphorothioate (Diazinon ® )

octachlorocamphene (toxaphene)

O-ethyl O-p-nitrophenyl phenylphosphonothioate (EPN)

cyano(3-phenoxyphenyl)-methyl-4-chloro-α-(1-methylethyl)-benzeneacetate (Pydrin ®) (3-phenoxyphenyl)methyl(±)-cis,trans-3-(2,2,-dichloroethenyl)-2,2-dimethylcyclopropanecarboxylate (Ambush ®)

O-ethyl-S-.(p-chlorophenyl)ethylphosphonodithioate (Curacron ®)

phosphorothiolothionic acid, O-ethyl-O-[4-(methylthio)phenyl]-S-n-propyl ester (Bolstar ®)

Fungicides:
methyl 2-benzimidazolecarbamate (carbendazim)
tetramethyl thiuram disulfide (thiram)
n-dodecylguanidine acetate (dodine)
manganese ethylenebisdithiocarbamate (maneb)
1,4-dichloro-2,5-dimethoxybenzene (chloroneb)

methyl 1-(butylcarbamoyl)-2-benzimidazolecarbamate (benomyl)

2-cyano-N-ethylcarbamoyl-2-methoxyiminoacetamide (Curzate®)

N-trichloromethylthiotetrahydrophthalimide (captan)

N-trichloromethylthiophthalimide (folpet)

Nematicides:

S-methyl 1-(dimethylcarbamoyl)-N-(methylcarbamoyloxy)thioformimidate (oxamyl)

S-methyl 1-carbamoyl-N-(methylcarbamoyloxy)thioformimidate

N-isopropylphosphoramidic acid, O-ethyl-O'-[4-(methylthio)-m-tolyl]diester (Nemacur®)

Bactericides:

tribasic copper sulfate streptomycin sulfate

Acaricides:

senecioic acid, ester with 2-sec-butyl-4,6-dinitrophenol (Morocide®)

6-methyl-1,3-dithiolo[2,3-B]quinonolin-2-one, (Morestan®) ethyl 4,4'-dichlorobenzilate (Chlorobenzilate®)

1,1-bis(p-chlorophenyl)-2,2,2-trichloroethanol (Kelthane®) bis(pentochloro-2,4-cyclopentadien-lyl) (Pentac®) tricyclohexyl trihydroxide (Plictran®)

EXAMPLE 10

The foliage only of red kidney bean plants in the two-leaf stage were sprayed to run-off with dispersions of compounds of this invention at various concentrations. Dispersions were prepared by dissolving appropriately weighed quantities of the active ingredient in 10 ml of acetone and diluting to 100 ml with water containing a surface active agent (Duponol® L-144 WDG) at 1:3000. After drying, leaves were excised and placed in covered 10 cm petri dishes along with moist filter paper to keep them fresh. Ten southern armyworm larvae were placed in each dish. Tests were run in duplicate. The units were kept in a room maintained at 25°±2° C., 53±5% RH. Results were recorded at the end of 2 days.

TABLE 10

| Compound | % a.i.[1] Spray Concentration | % Mortality |
|---|---|---|
| Methyl N-[[[N-[[N-[3,5-bis(1,1-dimethylethyl)-4-oxo-2,5-cyclohexadien-1-ylideneaminooxycarbonyl]-N-methylaminothio]]-N-methylaminocarbonyloxy]]]-ethanamidothioate | .005 .0025 | 100 90 |

[1] a.i. means active ingredient

EXAMPLE 11

The foliage of red kidney bean plants in the two-leaf stage was sprayed to run-off with dispersions of compounds of this invention at various concentrations. Dispersions were prepared by dissolving appropriately weighed quantities of the active ingredient in 10 ml of acetone and diluting to 100 ml with water containing a surface active agent (Duponol® L-144 WDG) at 1:3000. After drying, plants were placed under artificial light in a room maintained at 25°±2° C., 54±5% RH. After the designated period, leaves were excised and placed in covered 10 cm petri dishes along with moist filter paper to keep them fresh. Ten southern armyworm larvae were placed in each dish. These were run in duplicate. The units kept in a room maintained at 25°±2° C., 54±5% RH. Results were recorded 2 days after larvae were placed on the treated foliage.

TABLE 11

| | % a.i. Spray Concentration | % Mortality (2 days) | |
|---|---|---|---|
| Compound | | 2 Days Residual | 7 Days Residual |
| Methyl N-[[[N-[[N-[3,5-bis(1,1-dimethylethyl)-4-oxo-2,5-cyclohexadien-1-ylideneaminooxycarbonyl]-N-methylaminothio]]-N-methylaminocarbonyloxy]]]-ethanamidothioate | 0.01 0.005 | 100 80 | 95 75 |

EXAMPLE 12

Potted Stoneville 213 cotton plants approximately 25 cm high having 3-4 true leaves were sprayed to run-off with aqueous dispersions of compounds of this invention at 500 ppm. The sprays contained a surface active agent (Duponol® L-144 WDG) at a concentration of 1:3000. Another set of plants was similarly treated with methomyl. After drying, the plants were set out in the greenhouse and held for observation. Results were recorded after 5 days.

TABLE 12

| Compound (500 ppm a.i.)[1] | Rating[2] (5 Days) |
|---|---|
| Methyl N-[[[N-[[N-[3,5-bis(1,1-dimethylethyl)-4-oxo-2,5-cyclohexadien-1-ylideneaminooxycarbonyl]-N-methylaminothio]]-N-methylaminocarbonyloxy]]]-ethanamidothioate | 0 |
| Methyl O-(methylcarbamoyl)-thiolacetohydroxamate (methomyl) | 3R |
| Untreated Control | 0 |

[1] a.i. - active ingredient
[2] "R" denotes typical methomyl effective, i.e., reddening of older leaves, slight puckering and black stippling of younger leaves. Rating is on the basis of 0–10 with 0 indicating no effect and 10 indicating total leaf area involvement.

EXAMPLE 13

The foliage only of red kidney bean plants in the two-leaf stage were sprayed to run-off with dispersions of compounds of this invention at various concentrations. Dispersions were prepared by dissolving appropriately weighed quantities of the active ingredient in 10 ml of acetone and diluting to 100 ml with water containing a surface active agent (Duponol® L-144 WDG) at 1:3000. After drying, leaves were excised and placed in covered 10 cm petri dishes along with moist filter paper to keep them fresh. Ten southern armyworm larvae were placed in each dish. Tests were run in duplicate. The units were kept in a room maintained at 25°±2° C., 55±5% RH. Results were recorded at the end of 2 days.

TABLE 13

| | % Mortality (2 days) | |
|---|---|---|
| Compound | 0.01% A.I. | 0.005% A.I. |
| Methyl N-[[[N-[[N-[3,5-bis-(1,1-dimethylethyl)-4-oxo-2,5-cyclohexadien-1-ylideneaminooxycarbonyl]-N-methylaminothio]]-N-methylaminocarbonyloxo]]]- | — | 100 |

TABLE 13-continued

| | % Mortality (2 days) | |
|---|---|---|
| Compound | 0.01% A.I. | 0.005% A.I. |
| ethanamidothioate | — | — |
| Methyl N-[N-[N-(3,5-dimethyl-4-oxo-2,5-cyclohexadien-1-ylideneaminooxycarbonyl)-N-methylaminothio]-N-methylaminocarbonyloxy]ethanimidothioate | 100 | |
| Methyl N-[N-methyl-N-[N-methyl-N-[2-methyl-5-(1-methylethyl)-4-oxo-2,5-cyclohexadien-1-ylideneaminooxycarbonyl]aminothio]-aminocarbonyloxy]ethanimidothioate | 95 | — |
| Methyl N-[N-[N-[3,5-bis(1-methylethyl)-4-oxo-2,5-cyclohexadien-1-ylideneaminooxycarbonyl]-N-methylaminothio]-N-methylcarbonyloxy]-ethanimidothioate | — | 90 |
| Methyl N-[N-[N-[3,5-bis(1-methylethyl-4-oxo-2,5-cyclohexadien-1-ylideneaminooxycarbonyl]-N-methylaminothio]-N-methylcarbonyloxy]-ethanimidothioage | 100 | — |
| Methyl N-[N-[N-[2,5-bis(1,1-dimethylethyl)-4-oxo-2,5-cyclohexadien-1-ylideneamino-oxycarbonyl]-N-methylaminothio]-N-methylaminocarbonyloxy]ethanimidothioate | — | 100 |
| Methyl N-[N-[N-[5-(1,1-dimethylethyl)-2-methyl-4-oxo-2,5-cyclohexadien-1-ylidene-aminooxycarbonyl]-N-methylaminothio]-N-methylaminocarbonyloxy]ethanimidothioate | — | 95 |
| Methyl N-[N-[N-[3,5-bis(1,1-dimethylethyl)-6-oxo-2,4-cyclohexadien-1-ylidene-aminooxycarbonyl-N-methyl-aminothio]-N-methylamino-carbonyloxy]ethanimidothioate | — | 95 |
| Methyl N-[N-methyl-N-[N-methyl-N-(2,3,5,6-tetramethyl-4-oxo-2,5-cyclohexadien-1-ylidene-aminooxycarbonyl]aminothio]-aminocarbonyloxy]ethanimido-thioate | — | 100 |
| Methyl N-[N-methyl-N-[N-methyl-N-(4-oxo-2,5-cyclohexadien-1-ylideneaminooxycarbonyl)-aminothio]aminocarbonyloxy]ethanimidothioate | — | 100 |
| Methyl N-[N-[N-(3,5-dichloro-4-oxo-2,5-cyclohexadien-1-ylideneaminooxycarbonyl)-N-methylaminothio]-N-methyl-aminocarbonyloxy]ethanimido-thioate | 100 | — |
| Methyl N-[N-[N-(2,5-dimethyl-4-oxo-2,5-cyclohexadien-1-yl-ideneaminooxycarbonyl)-N-methylaminothioate]-N-methyl-aminocarbonyloxy]ethanimido-thioate | 100 | — |

EXAMPLE 14

Tobacco budworm, *Heliothis virescens*, larvae were treated topically with compounds of this invention. One microliter of each concentration used was applied to the dorsoprothoracic area of each larva tested. The stock solutions were prepared by dissolving appropriately weighed quantities of active ingredient in predetermined quantities of acetone. Further diluting with acetone yielded the desired conentrations. Larvae were treated in the individual 1 oz. cups in which they were reared on artificial diet. Fifteen larvae were treated with the desired concentration and kept in a growth room at 26°±0.5° C. and 50–60% RH. Mortality readings were taken at 48 hours.

TABLE 14

| Compound | % Mortality (48 hours) 0.25 μg/larva |
|---|---|
| Methyl N-[[[N-[[N-[3,5-bis(1,1-dimet-ylethyl)-4-oxo-2,5-cyclo-hexadien-1-ylideneaminooxy-carbonyl]-N-methylaminothio]]-N-methylaminocarbonyloxy]]]-ethanamidothioate | 83 |
| Methyl N-[N-[N-(3,5-dimethyl-4-oxo-2,5-cyclohexadien-1-yl-ideneaminooxycarbonyl)-N-methyl-aminothio]-N-methylaminocar-bonyloxy]ethanimidothioate | 87 |

EXAMPLE 15

Stems of nasturium leaves infested with black bean aphid, *Aphis fabae*, were placed in individual vials containing aqueous dispersions of compounds of this invention at various concentrations. Dispersions were prepared by dissolving appropriately weighed quantities of the active ingredient in 10 ml of acetone and diluting to 100 ml with water containing a surface active agent (Duponol® 1-144 WDG) at 1:3000. The units were kept in a room maintained at 25°±2° C., 55±5% RH. Results were recorded at the end of 1 day.

TABLE 15

| | % Mortality (1 day) % a.i. Spray concentration | |
|---|---|---|
| Compound | 0.005 | 0.0025 |
| Methyl N-[[[N-[[N-[3,5-bis(1,1-dimethylethyl)-4-oxo-2,5-cylco-hexadien-1-ylideneaminooxy-carbonyl]-N-methylaminothio] ]-N-methylaminocarbonyloxy]]-ethanamidothioate | 84 | — |
| Methyl N-[N-methyl-N-[N-methyl-N-[2-methyl-5-(1-methylethyl)-4-oxo-2,5-cyclohexadien-1-yl-ideneaminooxycarbonyl]amino-thio]aminocarbonyloxy]-ethanimidothioate | — | 100 |
| Methyl N-[N-[N-[3,5-bis(1-methylpropyl)-4-oxo-2,5-cyclohexadien-1-ylideneamino-oxycarbonyl]-N-methylamino-thio]-N-methylaminocarbonyl-oxy]ethanimidothioate | 93 | — |

EXAMPLE 16

Nasturtium leaves, infested with black bean aphid, *Aphis fabae*, were placed in individual vials of water. The leaves were sprayed to runoff with dispersions of compounds of this invention at various concentrations. Dispersions were prepared by dissolving appropriately weighed quantities of the active ingredient in 10 ml of acetone and diluting to 100 ml with water containing a surface active agent (Duponol® L-144 WDG) at 1:3000. The units were kept in a room maintained at 25°±2° C., 55±5% RH. Results were recorded at the end of 1 day.

TABLE 16

| Compound | % Mortality (1 day) % A.I. Concentration | |
|---|---|---|
| | 0.005 | 0.0025 |
| Methyl N-[N-methyl-N-[N-methyl-N-[2-methyl-5-(1-methylethyl)-4-oxo-2,5-cyclohexadien-1-yl-ideneaminooxycarbonyl]amino-thio]aminocarbonyloxy]-ethanimidothioate | — | 100 |
| Methyl N-[N-[N-[3,5-bis(1-methylpropyl)-4-oxo-2,5-cyclohexadien-1-ylidene-aminooxycarbonyl]-N-methyl-aminothio]-N-methylamino-carbonyloxy]ethanimidothioate | 99 | — |

What is claimed is:

1. A compound of the formula

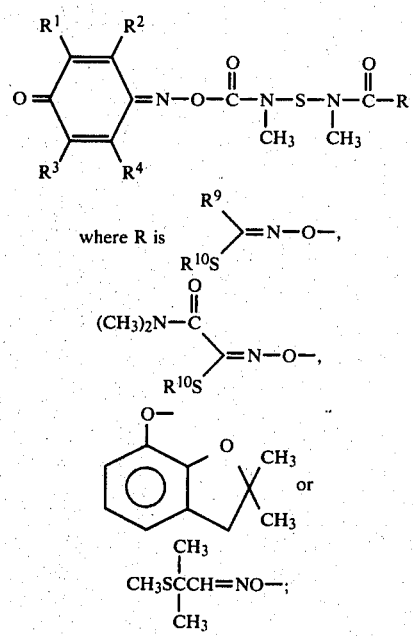

$R^1$, $R^2$, $R^3$, and $R^4$ are independently H, F, Cl, Br, $NO_2$, CN, $CF_3$, $C_1$-$C_{12}$ alkyl, $C_1$-$C_4$ alkoxy, or $COR^5$;
$R^5$ is $OR^6$ or $NR^7R^8$;
$R^6$ is $C_1$-$C_4$ alkyl;
$R^7$ is $C_1$-$C_4$ alkyl or methoxy;
$R^8$ is $C_1$-$C_4$ alkyl;
$R^9$ and $R^{10}$ are independently methyl or ethyl; or
$R^1$ and $R^2$ are taken together to form

—CH=CH—CH=CH—;

provided that:
(1) The total of $R^9$ and $R^{10}$ is not greater than three carbon atoms;
(2) Only one of $R^1$, $R^2$, $R^3$ and $R^4$ can be CN, $NO_2$, $COR^5$, or $CF_3$;
(3) If $R^2$ and $R^4$ are both alkyl, then $R^2$ and $R^4$ are independently $CH_3$ or $CH_2CH_3$;
(4) If any two of $R^1$, $R^2$, $R^3$, and $R^4$ are independently halogen or alkoxy, then the other two are independently hydrogen or $CH_3$;
(5) The total number of carbons $R^1$ to $R^4$ is not greater than 26;
(6) If $R^1$ and $R^2$ are both alkyl, then $R^2$ must be $CH_3$ or $CH_2CH_3$;
(7) If $R^3$ and $R^4$ are both alkyl, then $R^4$ must be $CH_3$ or $CH_2CH_3$.

2. A compound of the Formula

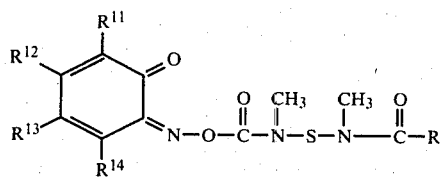

where R is

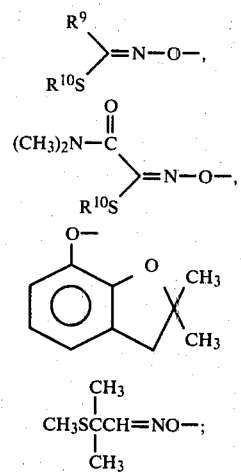

$R^9$ and $R^{10}$ are independently methyl or ethyl;
$R^{11}$, $R^{12}$, $R^{13}$ and $R^{14}$ are independently, H, $C_1$-$C_{12}$ alkyl, $C_1$-$C_4$ alkoxy, Cl or Br; or
either $R^{11}$ and $R^{12}$ or $R^{13}$ and $R^{14}$ are taken together to form —CH=CH—CH=CH—;
provided that
(1) the total of $R^9$ and $R^{10}$ is not greater than three carbon atoms;
(2) if three or more of $R^{11}$, $R^{12}$, $R^{13}$ and $R^{14}$ are other than H, then any of $R^{11}$, $R^{12}$, $R^{13}$ and $R^{14}$ which is not H, is selected from $CH_3$ or Cl, except that if $R^{11}$ and $R^{12}$ or $R^{13}$ and $R^{14}$ form the bridge —CH=CH—CH=CH—, then the remaining $R^{11}$ to $R^{14}$ groups are chosen from all definitions of $R^{11}$ to $R^{14}$;
(3) if any of $R^{11}$, $R^{12}$, $R^{13}$ and $R^{14}$ is secondary alkyl, tertiary alkyl or tertiary alkoxy, the adjacent group which is at least one of $R^{11}$, $R^{12}$, $R^{13}$ or $R^{14}$ must be selected from H, $CH_3$ or $CH_2CH_3$;
(4) the total number of carbons of $R^{11}$ to $R^{14}$ is not greater than 16.

3. The compound of claim 1 where
$R^1$ and $R^4$ are independently H, Cl, F, $C_1$-$C_5$ alkyl, $C_1$-$C_3$ alkoxy, or $CO_2R_6$ where $R^6$ is $C_1$-$C_4$ alkyl; and
$R^{11}$ to $R^{14}$ are independently H, Cl, $C_1$-$C_5$ alkyl and $C_1$-$C_3$ alkoxy.

4. The compound of claim 3 where $R^9$ and $R^{10}$ are $CH_3$.

5. The compound of claim 4 where
$R^2$ and $R^4$ are H,
$R^1$ and $R^3$ are independently $C_1$-$C_5$ alkyl,
$R^{12}$ and $R^{14}$ are H, and
$R^{11}$ and $R^{13}$ are independently $C_1$-$C_5$ alkyl.

6. The compound of claim 2 where $R^1$ and $R^4$ are independently H, Cl, F, $C_1$–$C_5$ alkyl, $C_1$–$C_3$ alkoxy, or $CO_2R_6$ where $R^6$ is $C_1$–$C_4$ alkyl; and $R^{11}$ to $R^{14}$ are independently H, Cl, $C_1$–$C_5$ alkyl and $C_1$–$C_3$ alkoxy.

7. The compound of claim 6 where $R^9$ and $R^{10}$ are $CH_3$.

8. The compound of claim 7 where
$R^2$ and $R^4$ are H,
$R^1$ and $R^3$ are independently $C_1$–$C_3$ alkyl,
$R^{12}$ and $R^{14}$ are H, and
$R^{11}$ and $R^{13}$ are independently $C_1$–$C_5$ alkyl.

9. The compound of claim 1 which is N-[[[N-[[N-[3,5-bis(1,1-dimethylethyl)-4-oxo-2,5-cyclohexadien-1-ylideneaminooxycarbonyl]-N-methylaminothio]]-N-methylaminocarbonyloxy]]]ethanimidothioic acid, methyl ester.

10. The compound of claim 1 which is N-[N-[N-(3,5-dimethyl-4-oxo-2,5-cyclohexadien-1-ylideneaminooxycarbonyl)-N-methylaminothio]-N-methylaminocarbonyloxy]ethanimidothioic acid, methyl ester.

11. The compound of claim 1 which is N-[N-methyl-N-[N-methyl-N-[2-methyl-5-(1-methylethyl)-4-oxo-2,5-cyclohexadien-1-ylideneaminooxycarbonyl]aminothio]aminocarbonyloxy]ethanimidothioic acid, methyl ester.

12. The compound of claim 1 which is N-[N-[N-[3,5-bis(1-methylpropyl)-4-oxo-2,5-cyclohexadien-lylideneaminooxycarbonyl]-N-methylaminothio]-N-methylaminocarbonyloxy]ethanimidothioic acid, methyl ester.

13. The compound of claim 1 which is N-[N-[N-[3,5-bis(1-methylethyl)-4-oxo-2,5-cyclohexadien-lylideneaminooxycarbonyl]-N-methylaminothio]-N-methylcarbonyloxy]ethanimidothioic acid, methyl ester.

14. The compound of claim 2 which is
methyl N-[N-[N-[[3,5-bis(1,1-dimethylethyl)-6-oxo-2,4-cyclohexadien-1-ylidene]aminoxycarbonyl]-N-methylaminothio]-N-methylaminocarbonyloxy]ethanimidothioate.

15. The compound of claim 1 which is
methyl N-[N-[N-[(3-dodecyl-1,4-dihydro-4-oxo-1-naphthalenylidene)aminooxycarbonyl]-N-methylaminothio]-N-methylaminocarbonyloxy]ethanimidothioate.

16. The compound of claim 2 which is
methyl N-[N-[N-[(1,2-dihydro-1-oxo-2-naphthalenylidene)aminooxycarbonyl]-N-methylaminothio]-N-methylaminocarbonyloxy]ethanimidothioate.

17. The compound of claim 1 which is
methyl N-[N-[N-[(1,4-dihydro-3-methyl-4-oxo-1-naphthalenylidene)aminooxycarbonyl]-N-methylaminothio]-N-methylaminocarbonyloxy]-ethanimidothioate.

18. An agricultural composition for insecticidal use consisting essentially of a surfactant, diluent or combinations thereof and a compound of claim 1.

19. An agricultural composition for insecticidal use consisting essentially of a surfactant, diluent or combinations thereof and a compound of claim 2.

20. An agricultural composition for insecticidal use consisting essentially of a surfactant, diluent or combinations thereof and a compound of claim 3.

21. An agricultural composition for insecticidal use consisting essentially of a surfactant, diluent or combinations thereof and a compound of claim 4.

22. An agricultural composition for insecticidal use consisting essentially of a surfactant, diluent or combinations thereof and a compound of claim 5.

23. An agricultural composition for insecticidal use consisting essentially of a surfactant, diluent or combinations thereof and a compound of claim 6.

24. An agricultural composition for insecticidal use consisting essentially of a surfactant, diluent or combinations thereof and a compound of claim 7.

25. An agricultural composition for insecticidal use consisting essentially of a surfactant, diluent or combinations thereof and a compound of claim 8.

26. An agricultural composition for insecticidal use consisting essentially of a surfactant, diluent or combinations thereof and a compound of claim 9.

27. An agricultural composition for insecticidal use consisting essentially of a surfactant, diluent or combinations thereof and the compound of claim 10.

28. An agricultural composition for insecticidal use consisting essentially of a surfactant, diluent or combinations thereof and the compound of claim 11.

29. An agricultural composition for insecticidal use consisting essentially of a surfactant, diluent or combinations thereof and the compound of claim 12.

30. An agricultural composition for insecticidal use consisting essentially of a surfactant, diluent or combinations thereof and the compound of claim 13.

31. An agricultural composition for insecticidal use consisting essentially of a surfactant, diluent or combinations thereof and the compound of claim 14.

32. An agricultural composition for insecticidal use consisting essentially of a surfactant, diluent or combinations thereof and the compound of claim 15.

33. An agricultural composition for insecticidal use consisting essentially of a surfactant, diluent or combinations thereof and the compound of claim 16.

34. An agricultural composition for insecticidal use consisting essentially of a surfactant, diluent or combinations thereof and the compound of claim 17.

35. A method for control of insects which comprises applying to a locus to be protected an insecticidally effective amount of a compound of claim 1.

36. A method for control of insects which comprises applying to a locus to be protected an insecticidally effective amount of a compound of claim 2.

37. A method for control of insects which comprises applying to a locus to be protected an insecticidally effective amount of a compound of claim 3.

38. A method for control of insects which comprises applying to a locus to be protected an insecticidally effective amount of a compound of claim 4.

39. A method for control of insects which comprises applying to a locus to be protected an insecticidally effective amount of of claim 5.

40. A method for control of insects which comprises applying to a locus to be protected an insecticidally effective amount of of claim 6.

41. A method for control of insects which comprises applying to a locus to be protected an insecticidally effective amount of of claim 7.

42. A method for control of insects which comprises applying to a locus to be protected an insecticidally effective amount of a compound of of claim 8.

43. A method for control of insects which comprises applying to a locus to be protected an insecticidally effective amount of a compound of of claim 9.

44. A method for control of insects which comprises applying to a locus to be protected an insecticidally effective amount of the compound of claim 10.

45. A method for control of insects which comprises applying to a locus to be protected an insecticidally effective amount of the compound of claim 11.

46. A method for control of insects which comprises applying to a locus to be protected an insecticidally effective amount of the compound of claim 12.

47. A method for control of insects which comprises applying to a locus to be protected an insecticidally effective amount of the compound of claim 13.

48. A method for control of insects which comprises applying to a locus to be protected an insecticidally effective amount of the compound of claim 14.

49. A method for control of insects which comprises applying to a locus to be protected an insecticidally effective amount of the compound of claim 15.

50. A method for control of insects which comprises applying to a locus to be protected an insecticidally effective amount of the compound of claim 16.

51. A method for control of insects which comprises applying to a locus to be protected an insecticidally effective amount of the compound of claim 17.

52. A compound of the formula

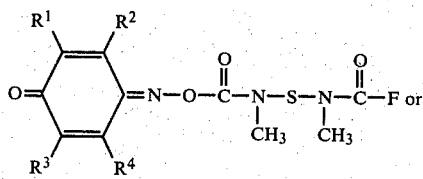

-continued

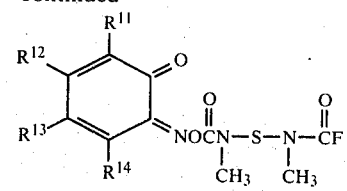

$R^1$, $R^2$, $R^3$, and $R^4$ are independently H, F, Cl, Br, $NO_2$, CN, $CF_3$, $C_1$-$C_{12}$ alkyl, $C_1$-$C_4$ alkoxy, or $COR^5$;

$R^5$ is $OR^6$ or $NR^7R^8$;

$R^6$ is $C_1$-$C_4$ alkyl;

$R^7$ is $C_1$-$C_4$ alkyl or methoxy;

$R^8$ is $C_1$-$C_4$ alkyl; or $R^1$ and $R^2$ are taken together to form

—CH=CH—CH=CH—;

$R^{11}$, $R^{12}$, $R^{13}$ and $R^{14}$ are independently, H, $C_1$-$C_{12}$ alkyl, $C_1$-$C_4$ alkoxy, Cl or Br; or either $R^{11}$ and $R^{12}$ or $R^{13}$ and $R^{14}$ are taken together to form —CH=CH—CH=CH—;

provided that:

(1) Only one of $R^1$, $R^2$, $R^3$ and $R^4$ can be CN, $NO_2$, $COR^5$, or $CF_3$;

(2) If $R^2$ and $R^4$ are both alkyl, then $R^2$ and $R^4$ are independently $CH_3$ or $CH_2CH_3$;

(3) If any two of $R^1$, $R^2$, $R^3$, and $R^4$ are independently halogen or alkoxy, then the other two are independently hydrogen or $CH_3$;

(4) The total number of carbons $R^1$ to $R^4$ is not greater than 26;

(5) If $R^1$ and $R^2$ are both alkyl, then $R^2$ must be $CH_3$ or $CH_2CH_3$;

(6) If $R^3$ and $R^4$ are both alkyl, then $R^4$ must be $CH_3$ or $CH_2CH_3$;

(7) if three or more of $R^{11}$, $R^{12}$, $R^{13}$ and $R^{14}$ are other than H, then any of $R^{11}$, $R^{12}$, $R^{13}$ and $R^{14}$ which is not H is selected from $CH_3$ or Cl, except that if $R^{11}$ and $R^{12}$ or $R^{13}$ and $R^{14}$ form the bridge —CH=CH—CH=CH—, then the remaining $R^{11}$ to $R^{14}$ groups are chosen from all definitions of $R^{11}$ to $R^{14}$;

(8) if any of $R^{11}$, $R^{12}$, $R^{13}$ and $R^{14}$ is secondary alkyl, tertiary alkyl or tertiary alkoxy, the adjacent group which is at least one of $R^{11}$, $R^{12}$, $R^{13}$ or $R^{14}$ must be selected from H, $CH_3$ or $CH_2CH_3$;

(9) the total number of carbons of $R^{11}$ to $R^{14}$ is not greater than 16.

* * * * *